(12) United States Patent
Messinger et al.

(10) Patent No.: US 10,939,977 B2
(45) Date of Patent: Mar. 9, 2021

(54) POSITIONING MARKER

(71) Applicant: Augmedics Ltd., Yokneam Illit (IL)

(72) Inventors: Daniel Messinger, Migdal Haemek (IL); Stuart Wolf, Yokneam (IL); Nissan Elimelech, Beerotaim (IL)

(73) Assignee: AUGMEDICS LTD., Yokneam Illit (IL)

( * ) Notice: Subject to any disclaimer, the term of this patent is extended or adjusted under 35 U.S.C. 154(b) by 111 days.

(21) Appl. No.: 16/199,281

(22) Filed: Nov. 26, 2018

(65) Prior Publication Data

US 2020/0163739 A1    May 28, 2020

(51) Int. Cl.
*G06K 7/10* (2006.01)
*A61B 90/00* (2016.01)
*A61B 34/20* (2016.01)

(52) U.S. Cl.
CPC .............. *A61B 90/39* (2016.02); *A61B 34/20* (2016.02); *A61B 90/36* (2016.02); *A61B 2090/3937* (2016.02); *A61B 2090/3966* (2016.02)

(58) Field of Classification Search
CPC ......... A61B 90/03; A61B 90/36; A61B 96/39; A61B 34/20; A61B 34/30; A61B 2090/3966; A61B 2090/3937; A61B 2090/3983; A61B 2090/3945; A61B 2034/2055; G02B 5/136; G02B 27/017; G02B 27/32; G02B 27/34; G06T 7/33; G06T 7/73; G06T 7/80; G06T 7/246
See application file for complete search history.

(56) References Cited

U.S. PATENT DOCUMENTS

| | | |
|---|---|---|
| 4,863,238 A | 9/1989 | Brewster |
| 5,441,042 A | 8/1995 | Putman |
| 5,792,046 A | 8/1998 | Dobrovolny |
| 5,841,507 A | 11/1998 | Barnes et al. |
| 6,006,126 A | 12/1999 | Cosman |
| 6,256,529 B1 | 7/2001 | Holupka et al. |
| 6,314,310 B1 | 11/2001 | Ben-Haim et al. |
| 6,609,022 B2 | 8/2003 | Vilsmeier et al. |
| 6,610,009 B2 | 8/2003 | Person |
| 6,675,040 B1 | 1/2004 | Cosman |
| 6,757,068 B2 | 6/2004 | Foxlin |
| 6,856,826 B2 | 2/2005 | Seeley et al. |
| 6,891,518 B2 | 5/2005 | Sauer et al. |
| 6,919,867 B2 | 7/2005 | Sauer |
| 7,043,961 B2 | 5/2006 | Pandey et al. |

(Continued)

FOREIGN PATENT DOCUMENTS

| | | |
|---|---|---|
| CN | 103106348 A | 5/2013 |
| DE | 202004011567 U1 | 11/2004 |

(Continued)

OTHER PUBLICATIONS

U.S. Appl. No. 16/419,023 office action dated Oct. 4, 2019.

(Continued)

*Primary Examiner* — Mustak Choudhury
(74) *Attorney, Agent, or Firm* — Kligler & Associates Patent Attorneys Ltd

(57) ABSTRACT

A positioning marker, consisting of a base having a retroreflective surface. The marker also has a cover, which is fitted over and fastened to the base and has a plurality of openings through which the retroreflective surface is visible.

22 Claims, 6 Drawing Sheets

VIEW FROM BELOW

(56) References Cited

U.S. PATENT DOCUMENTS

| | | |
|---|---|---|
| 7,107,091 B2 | 9/2006 | Jutras et al. |
| 7,171,255 B2 | 1/2007 | Holupka et al. |
| 7,229,078 B2 | 6/2007 | Lechot |
| 7,320,556 B2 | 1/2008 | Vagn-Erik |
| 7,364,314 B2 | 4/2008 | Nilsen et al. |
| 7,435,219 B2 | 10/2008 | Kim |
| 7,493,153 B2 | 2/2009 | Ahmed et al. |
| 7,719,769 B2 | 5/2010 | Sugihara et al. |
| 7,769,236 B2 | 8/2010 | Fiala |
| 7,774,044 B2 | 8/2010 | Sauer et al. |
| 7,840,256 B2 | 11/2010 | Lakin et al. |
| 7,857,271 B2 | 12/2010 | Lees |
| 7,874,686 B2 | 1/2011 | Rossner et al. |
| 7,881,770 B2 | 2/2011 | Melkent et al. |
| 7,993,353 B2 | 8/2011 | Robner et al. |
| 8,271,069 B2 | 9/2012 | Jascob et al. |
| 8,386,022 B2 | 2/2013 | Jutras et al. |
| 8,692,845 B2 | 4/2014 | Fedorovskaya et al. |
| 8,836,768 B1 | 9/2014 | Rafii et al. |
| 8,848,977 B2 | 9/2014 | Bammer et al. |
| 8,950,877 B2 | 2/2015 | Northey et al. |
| 9,149,317 B2 | 10/2015 | Arthur et al. |
| 9,179,984 B2 | 11/2015 | Teichman et al. |
| 9,220,573 B2 | 12/2015 | Kendrick et al. |
| 9,378,558 B2 | 6/2016 | Kajiwara et al. |
| 9,456,878 B2 | 10/2016 | Macfarlane et al. |
| 9,495,585 B2 | 11/2016 | Bicer et al. |
| 9,498,231 B2 | 11/2016 | Haider et al. |
| 9,532,849 B2 | 1/2017 | Anderson et al. |
| 9,724,165 B2 | 8/2017 | Arata et al. |
| 9,844,413 B2 | 12/2017 | Daon et al. |
| 9,872,733 B2 | 1/2018 | Shoham et al. |
| 9,898,866 B2 | 2/2018 | Fuchs et al. |
| 9,928,629 B2 | 3/2018 | Benishti et al. |
| 9,943,374 B2 | 4/2018 | Merritt et al. |
| 10,022,104 B2 | 7/2018 | Sell et al. |
| 10,034,713 B2 | 7/2018 | Yang et al. |
| 10,080,616 B2 | 9/2018 | Wilkinson et al. |
| 10,085,709 B2 | 10/2018 | Lavallee et al. |
| 10,108,833 B2 | 10/2018 | Hong et al. |
| 10,134,166 B2 | 11/2018 | Benishti et al. |
| 10,166,079 B2 | 1/2019 | McLachlin et al. |
| 10,194,993 B2 | 2/2019 | Roger et al. |
| 10,251,724 B2 | 4/2019 | McLachlin et al. |
| 10,296,805 B2 | 5/2019 | Yang et al. |
| 10,420,626 B2 | 9/2019 | Tokuda et al. |
| 10,463,434 B2 | 11/2019 | Siegler et al. |
| 10,504,231 B2 | 12/2019 | Fiala |
| 10,537,395 B2 | 1/2020 | Perez |
| 2002/0082498 A1 | 6/2002 | Wendt et al. |
| 2003/0156144 A1 | 8/2003 | Morita |
| 2003/0210812 A1 | 11/2003 | Khamene et al. |
| 2004/0138556 A1 | 7/2004 | Cosman |
| 2005/0024586 A1 | 2/2005 | Teiwes et al. |
| 2005/0119639 A1 | 6/2005 | McCombs et al. |
| 2008/0007645 A1 | 1/2008 | McCutchen |
| 2008/0262812 A1 | 10/2008 | Arata et al. |
| 2009/0018437 A1 | 1/2009 | Cooke |
| 2009/0227847 A1 | 9/2009 | Tepper et al. |
| 2010/0149073 A1 | 6/2010 | Chaum et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0245625 A1 | 10/2011 | Trovato et al. |
| 2012/0014608 A1 | 1/2012 | Watanabe et al. |
| 2012/0068913 A1 | 3/2012 | Bar-Zeev et al. |
| 2012/0109151 A1 | 5/2012 | Maier-Hein et al. |
| 2012/0143050 A1 | 6/2012 | Heigl |
| 2012/0182605 A1 | 7/2012 | Hall et al. |
| 2012/0216411 A1 | 8/2012 | Wevers et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0249787 A1 | 9/2013 | Morimota |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300967 A1 | 10/2014 | Tilleman et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0340286 A1 | 11/2014 | Machida et al. |
| 2014/0361956 A1 | 12/2014 | Mikhailov et al. |
| 2015/0018672 A1 | 1/2015 | Blumhofer et al. |
| 2015/0070347 A1 | 3/2015 | Hofmann et al. |
| 2015/0150641 A1 | 6/2015 | Daon et al. |
| 2015/0297314 A1 | 10/2015 | Fowler et al. |
| 2015/0305828 A1 | 10/2015 | Park et al. |
| 2015/0351863 A1 | 12/2015 | Plassky et al. |
| 2015/0366620 A1 | 12/2015 | Cameron et al. |
| 2016/0103318 A1 | 4/2016 | Du et al. |
| 2016/0175064 A1 | 6/2016 | Stenile et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0256223 A1 | 9/2016 | Haimer et al. |
| 2016/0302870 A1 | 10/2016 | Wilkinson et al. |
| 2016/0324583 A1 | 11/2016 | Kheradpir et al. |
| 2016/0339337 A1 | 11/2016 | Ellsworth et al. |
| 2017/0076501 A1 | 3/2017 | Jagga et al. |
| 2017/0086941 A1* | 3/2017 | Marti ............... A61B 90/39 |
| 2017/0164919 A1 | 6/2017 | LaVallee et al. |
| 2017/0239015 A1 | 8/2017 | Sela et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0348055 A1 | 12/2017 | Salcedo et al. |
| 2017/0367766 A1 | 12/2017 | Mahfouz |
| 2018/0003981 A1 | 1/2018 | Urey |
| 2018/0018791 A1 | 1/2018 | Guoyi |
| 2018/0036884 A1* | 2/2018 | Chen ............... A61B 34/20 |
| 2018/0049622 A1 | 2/2018 | Ryan et al. |
| 2018/0116732 A1 | 5/2018 | Lin et al. |
| 2018/0153626 A1 | 6/2018 | Yang et al. |
| 2018/0185100 A1 | 7/2018 | Weinstein et al. |
| 2018/0193097 A1 | 7/2018 | McLachlin et al. |
| 2018/0200002 A1 | 7/2018 | Kostrzewski et al. |
| 2018/0262743 A1 | 9/2018 | Casas |
| 2018/0318035 A1 | 11/2018 | McLachlin et al. |
| 2019/0000372 A1 | 1/2019 | Gullotti et al. |
| 2019/0015163 A1 | 1/2019 | Abhari et al. |

(56) References Cited

U.S. PATENT DOCUMENTS

| | | | |
|---|---|---|---|
| 2019/0043238 | A1 | 2/2019 | Benishti et al. |
| 2019/0080515 | A1 | 3/2019 | Geri et al. |
| 2019/0192230 | A1 | 6/2019 | Siemionow et al. |
| 2020/0138518 | A1 | 5/2020 | Lang |
| 2020/0321099 | A1 | 10/2020 | Holladay et al. |
| 2020/0388075 | A1 | 12/2020 | Kazanzides et al. |

FOREIGN PATENT DOCUMENTS

| | | | |
|---|---|---|---|
| DE | 102014008153 | A1 | 10/2014 |
| EP | 1640750 | A1 | 3/2006 |
| EP | 3216416 | A1 | 9/2017 |
| GB | 2507314 | A | 4/2014 |
| KR | 20140120155 | A | 10/2014 |
| WO | 03034705 | A2 | 4/2003 |
| WO | 2007115826 | A2 | 10/2007 |
| WO | 2008103383 | A1 | 8/2008 |
| WO | 2010067267 | A1 | 6/2010 |
| WO | 2013112554 | A1 | 8/2013 |
| WO | 2014024188 | A1 | 2/2014 |
| WO | 2014037953 | A2 | 3/2014 |
| WO | 2014113455 | A1 | 7/2014 |
| WO | 2014125789 | A1 | 8/2014 |
| WO | 2014167563 | A1 | 10/2014 |
| WO | 2014174067 | A1 | 10/2014 |
| WO | 2015058816 | A1 | 4/2015 |

OTHER PUBLICATIONS

Fingas., "Fraunhofer iPad app guides liver surgery through augmented reality", pp. 1-6, Aug. 22, 2013.
U.S. Appl. No. 16/159,740 office action dated Jan. 25, 2019.
Lumus Ltd., "DK-32 See-through Wearable Display Development Kit", Rehovot, Israel, 2 pages, Dec. 24, 2013.
European Patent Application # 16767845.7 Office Action dated May 21, 2019.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data , pp. 1-4, Feb. 2019.
International Patent Application # PCT/IB2019/053524 search report dated Aug. 14, 2019.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
International Application # PCT/IB2019/059770 search report dated Mar. 17, 2020.
International Application # PCT/IB2019/059771 search report dated Mar. 1, 2020.
U.S. Appl. No. 16/419,023 Third party submission dated Jan. 19, 2020.
Sagitov et al., "Comparing Fiducial Marker Systems in the Presence of Occlusion", International Conference on Mechanical, System and Control Engineering (ICMSC), pp. 1-6, 2017.
Liu et al., "Marker orientation in fiducial registration", Medical Imaging 2003: Image Processing, Proceedings of SPIE vol. 5032, pp. 1176-1185, 2003.
U.S. Appl. No. 16/419,023 Office Action dated Sep. 3, 2020.
International Applicaton # PCT/IB2020/056893 Search Report dated Nov 9, 2020.
U.S. Appl. No. 16/200,144 Office Action dated Dec. 28, 2020.
International Application # PCT/IB2020/060017 Search Report dated Jan. 7, 2021.
U.S. Appl. No. 16/724,297 office action dated Jan 26, 2021.

* cited by examiner

VIEW FROM ABOVE

TOP VIEW

VIEW FROM BELOW

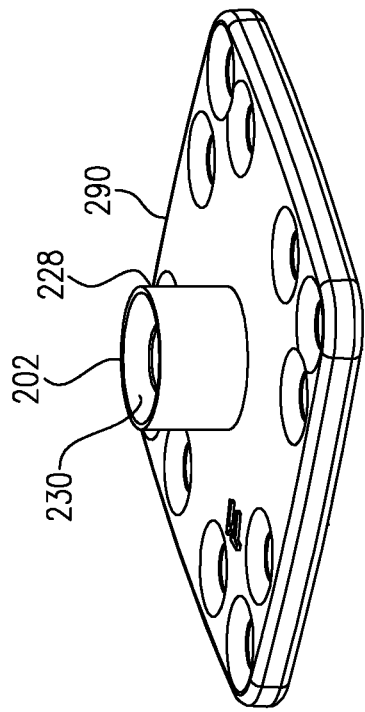
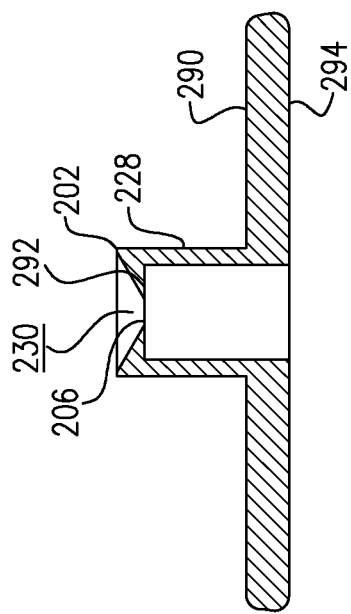
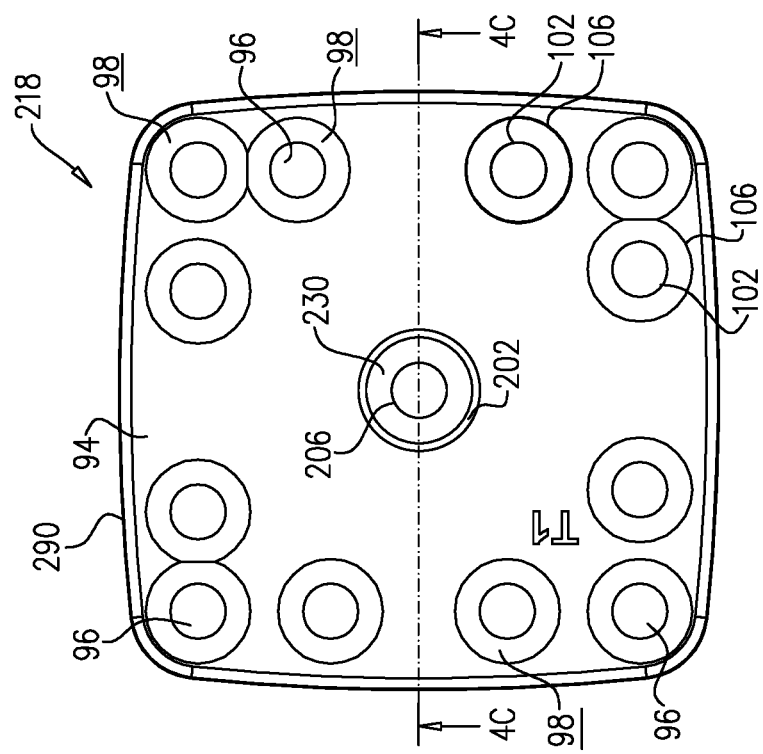

POSITIONING MARKER

FIELD OF THE INVENTION

The present invention relates generally to a fiducial marker, and specifically to a marker that can be tracked optically.

BACKGROUND OF THE INVENTION

During image guide surgery it is typically necessary to track objects used in the surgery, and/or elements of the patient undergoing the surgery. It may also be necessary to track and/or observe objects in other fields. A number of methods for performing such tracking or observation are known.

U.S. Pat. No. 4,863,238 to Brewster describes a reflective marker for marking an object such as a highway pole and the like by reflective light. The reflective marker comprises a support layer, and a top plate affixed thereto having die-cut portions adapted, when removed, to form openings which cooperate with the support layer to define shallow recesses in the marker.

U.S. Pat. No. 6,609,022 to Vilsmeier, et al. describes a method for supporting the treatment of a patient, including a navigation system detecting and tracking the positions of the patient, of his/her parts of the body, and of the target of the treatment and the treatment devices.

U.S. Pat. No. 7,364,314 to Nilsen, et al. describes optical structures and methods for manufacturing the same which include a substrate and a plurality of two-sided optical components disposed along the substrate. Retroreflective optical structures are also provided.

U.S. Pat. No. 7,874,686 to Rossner, et al. describes a reflective marker and a method for manufacturing the marker. The reflective marker includes an inner body and a reflective covering, and a reflective substance is applied to the inner body and forms the reflective covering together with pellets contained in the substance or applied after the substance has been applied.

U.S. Pat. No. 8,950,877 to Northey, et al. describes retroreflective sheeting that includes a first portion of prismatic retroreflective sheeting having a first cube corner structure that creates a first visual feature in the retroreflective sheeting and a second portion of prismatic retroreflective sheeting having a second cube corner structure.

US Patent Application 2011/0216411 to Reed, et al. describes retro-reflective sheeting comprising a flexible optical material film or substrate having a geometric optical surface opposite a base surface. The geometric optical surface includes a background pattern region of corner cubes arranged at a first orientation with respect to an edge of the retro-reflective sheeting.

US Patent Application 2012/0143050 to Heigl describes a reference foil comprising an unsymmetric marker foil device which includes spatially separated pieces of a marker material foil in an unsymmetric arrangement and/or at least one unsymmetric integral piece of the marker material foil. The reference foil and a carrier device for the same may be used for example in image-guided surgery.

US Patent Application 2012/0182605 to Hall, et al. describes passive infrared markers which are reflective in the thermal and/or near infrared wavebands.

US Patent Application 2015/0351863 to Plassky, et al. describes a marker for optical medical navigation, comprising a structure with at least one recess, and at least one supporting element, wherein each supporting element is configured to be accommodated within a particular recess.

US Patent Application 2016/0175064 to Steinle, et al. describes a medical navigation marker device comprising a light reflector, characterized in that the reflector features a marker pattern that points in more than one spatial direction.

German Patent DE202004011567 assigned to Aesculap AG describes how the position of a surgical instrument is defined by a marker integrated in the tool or a bone screw and is transmitted to a processing unit by infrared radiation reflected by a special element. The element is punched out of a suitable material preferably in a round shape and held in a frame located at the marker.

European Patent Application EP1640750A1 to Mosimann, et al. describes a retro-reflective device having at least a body comprising salient elements on an external surface of the body. The body is made of at least one first material entity made of a homogeneous compound of plastic material with on one hand elements entirely coated with at least one reflective layer and fully embedded inside the plastic material, and on the other hand salient elements partially coated with a same reflective layer.

PCT Patent Application WO2015058816 to Vasey, et al. describes a hybrid medical marker for use in a medical navigation system, the marker comprising a marker core which comprises a contrast medium and an outer surface which is at least partly light-reflective.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a positioning marker, including:

a base having a retroreflective surface; and a cover, which is fitted over and fastened to the base and has a plurality of openings through which the retroreflective surface is visible.

Typically, the openings are right conical frusta. The frusta may terminate in respective first shapes and second shapes smaller than the first shapes, and the second shapes contact the retroreflective surface when the cover is fastened to the base, forming respective retroreflectors. The respective retroreflectors may be arranged on a flat plane.

In a disclosed embodiment the retroreflective surface includes a base flat surface, and the cover includes a cover flat surface which mates with the base flat surface when the cover is fastened to the base, so that respective sections of the openings contact the retroreflective surface.

In a further disclosed embodiment the base includes a first sheet configured in a first plane, and the openings generate respective retroreflectors from the retroreflective surface and in the first plane when the cover is fastened to the base, the cover including a further opening, the marker including a second sheet having a further retroreflective surface configured in a second plane parallel to and distinct from the first plane, so that the further retroreflective surface is visible through the further opening when the cover is fastened to the base.

Typically, the further opening is a right conical frustum.

The base may include a central aperture, and the right conical frustum may penetrate the central aperture when the cover is fastened to the base.

Alternatively, there may a support protruding from the cover, the support including a support plane, aligned with the second plane, configured to fit to the second sheet.

A yet further disclosed embodiment may include a cover retainer which is configured to be fixedly connected to the cover and to retain the base in fixed contact with the cover, so as to fasten the base to the cover. Typically, the base includes a central aperture, the cover includes a first connecting element, and the cover retainer includes a second connecting element mating with the first connecting element so as to fasten the cover to the cover retainer and the base, and at least one of the connecting elements penetrates the central aperture.

In an alternative embodiment the retroreflective surface includes at least one of retroreflective tape and retroreflective paint.

There is further provided, according to an embodiment of the present invention, a method for producing a positioning marker, including:

forming a retroreflective surface on a base; and fitting a cover over and fastening the cover to the base, wherein the cover has a plurality of openings through which the retroreflective surface is visible.

The present disclosure will be more fully understood from the following detailed description of the embodiments thereof, taken together with the drawings, in which:

BRIEF DESCRIPTION OF THE DRAWINGS

FIGS. 4A, 4B, and 4C are schematic diagrams of a cover for a positioning marker, according to an alternative embodiment of the present invention.

DETAILED DESCRIPTION OF EMBODIMENTS

Overview

In an augmented reality environment, as well as in other environments, it is often necessary to register frames of reference of different elements of a system being used. For example, in the case of augmented reality, the frame of reference of an assembly mounted on the head of a user of an augmented reality system typically needs to be registered with the scene being viewed through the assembly.

Embodiments of the present invention provide a positioning marker which facilitates the registration referred to above, by enabling a processor coupled to the augmented reality assembly to track the marker, and to maintain the tracking even when large changes of angle, subtended by the marker to the assembly, occur.

The positioning marker comprises a base, typically in the form of a rectangular plane sheet with a central aperture, and the sheet has a retroreflective surface. A marker cover is fitted over and is fastened to the base, and the cover has a plurality of openings through which the retroreflective surface of the base is visible. The openings in the cover are typically in the form of right conical frusta, the conical shape of the openings allowing retroreflectors formed in the retroreflective surface by the openings to be visible even when the large changes of angle referred to above occur.

The retroreflectors are typically configured to be in a given plane, and in order to enhance the tracking provided by the marker, the marker may comprise a further retroreflector located in a plane different from the given plane. The further retroreflector may be formed by providing a further opening in the form of a right conical frustum in the cover, the frustum of the further opening having a different depth from the depth of the frusta described above. Having all the openings of the cover in the form of frusta enables the retroreflectors formed by the openings to be visible even when large changes of angle occur.

In order to fixedly fasten the cover to the base the marker typically comprises a cover retainer which can be fixedly attached to the cover while fastening the base to the cover. Typically the base is "sandwiched" between the cover retainer and the cover, and the further reflector is also sandwiched between the between the cover retainer and the cover.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
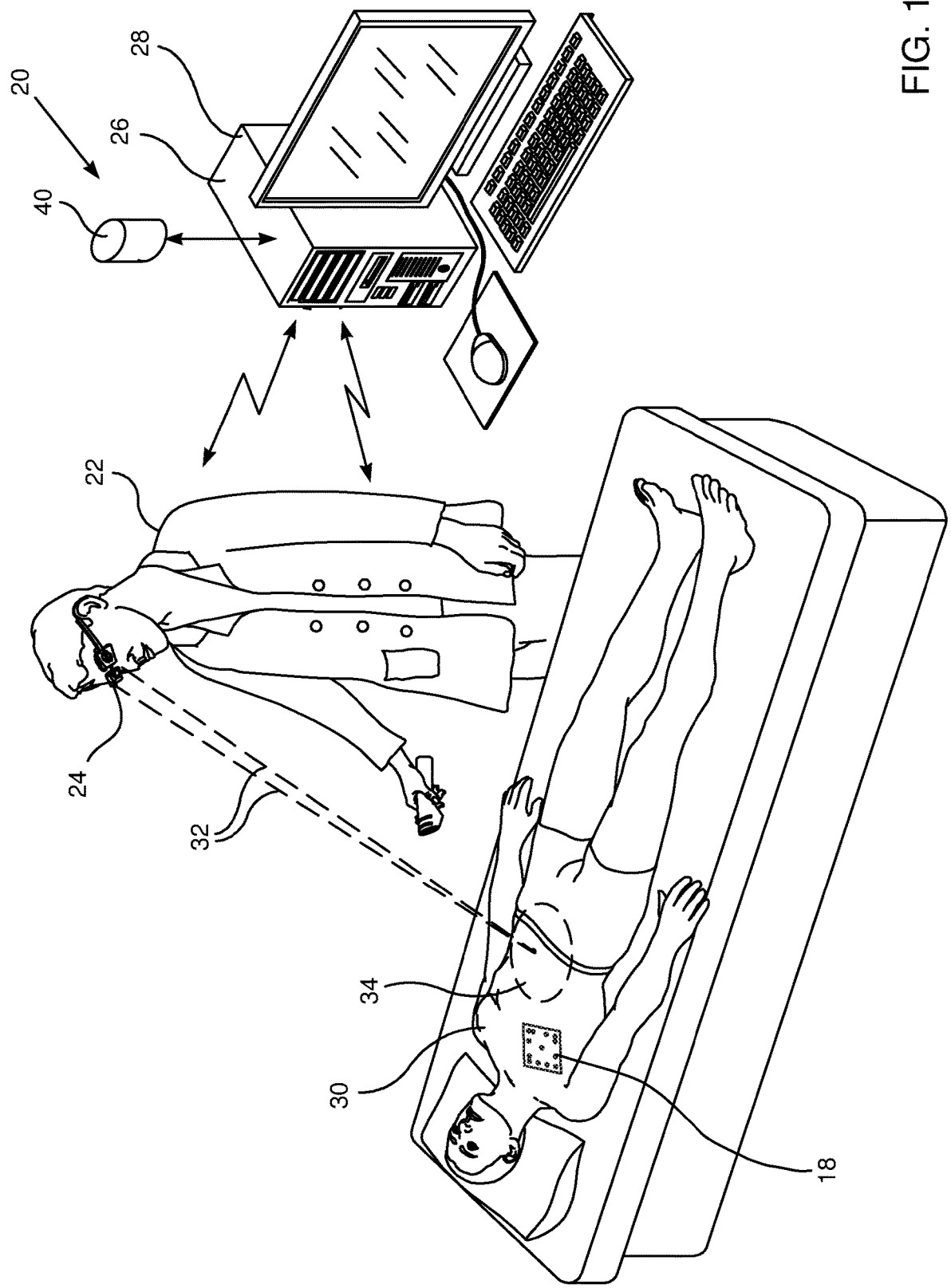
FIG. 1 schematically illustrates use of a positioning marker in an augmented reality system, according to an embodiment of the present invention.

Reference is now made to FIG. 1, which schematically illustrates use of a positioning marker 18 in an augmented reality system 20, according to an embodiment of the present invention. By way of example and for simplicity, in the following description system 20 is assumed to be used by a medical professional 22 in a medical procedure. However, it will be understood that embodiments of the present invention may be used in non-medical situations, such as in operating a video game, in simulating a real-world event, or in providing an aid to navigation.

System 20 is operated by medical professional 22, who wears an augmented reality assembly 24, described in more detail below with respect to FIG. 2. While assembly 24 may be incorporated for wearing into a number of different retaining structures on professional 22, in the present description the retaining structure is assumed to be similar to a pair of spectacles. Those having ordinary skill in the augmented reality art will be aware of other possible structures, such as incorporation of the augmented reality assembly into a head-up display that is integrated into a helmet worn by the user of system 20.

System 20 comprises and is under overall control of a processor 26. In one embodiment processor 26 is assumed to be incorporated within a stand-alone computer 28, and the processor typically communicates with other elements of the system, including assembly 24, wirelessly, as is illustrated in FIG. 1. Alternatively or additionally, processor 26 may use optical and/or conducting cables for communication. Further alternatively or additionally, processor 26 may be integrated within assembly 24, or in the mounting of the assembly. Processor 26 is typically able to access a database 40, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

The medical procedure exemplified here is on a patient 30, and during the procedure professional 22 gazes along gaze directions 32 at a region of interest (ROI) 34. ROI 34 typically, but not necessarily, comprises a portion of the patient. In embodiments of the present invention professional 22 enables processor 26 to identify the ROI by locating positioning marker 18, described in more detail below, at a predefined location with respect to ROI 34, e.g., the ROI may be a predefined distance to the right and a predefined distance below marker 18. As is also described below, processor 26 is able to track the location of marker 18, and thus, since the marker is at a predefined location with respect to ROI 34, the processor is able to track the location of the ROI.

Alternatively or additionally, positioning marker 18, or a marker substantially similar to marker 18, may be attached to a tool or other device used in the procedure. In this case processor 26 is able to track the marker and thus the tool or device attached to the marker. For clarity and simplicity, except where stated otherwise, in the following description marker 18 is assumed to be used as a stand-alone element for tracking ROI 34, but those having skill in the art will be able to adapt the description, mutatis mutandis, for the case when the marker is attached to a tool or other device to be tracked using the marker.

Figure 2:
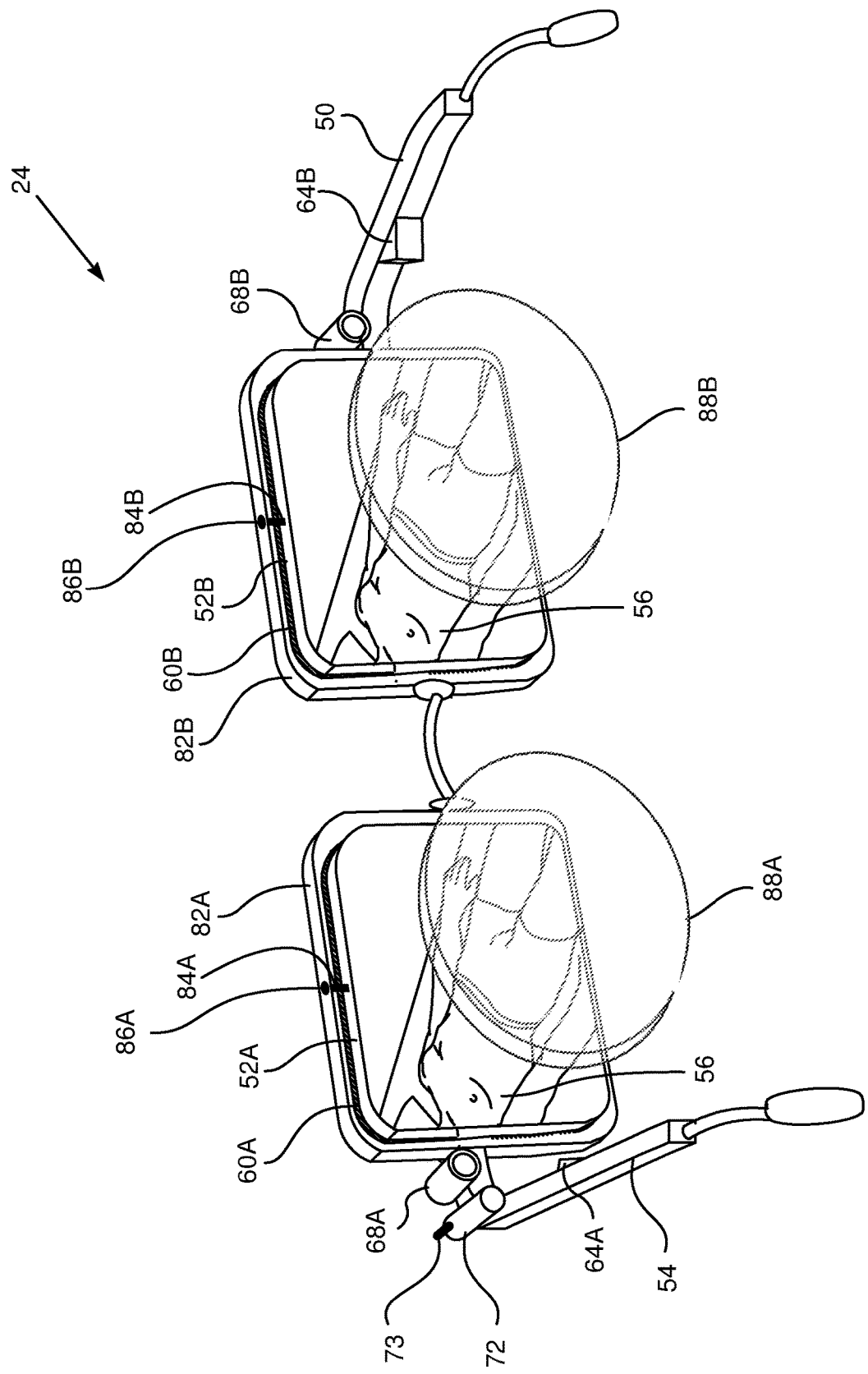
FIG. 2 is a schematic diagram illustrating an assembly used in the system, as well as functions that may be implemented in the assembly, according to an embodiment of the present invention.

FIG. 2 is a schematic diagram illustrating assembly 24, as well as functions that may be implemented in the assembly, according to an embodiment of the present invention. As stated above, assembly 24 is configured, by way of example, as a pair of spectacles 50. Similar elements of each "half" of the pair of spectacles are referred to generically by an identifying numeral, and the similar elements are differentiated as necessary by adding a letter to the numeral. Thus spectacles 50 comprise planar optical combiners 52, comprising combiners 52A and 52B in front of, respectively, the left and right eyes of professional 22. Optical combiners 52 are mounted on a retaining structure 54 which holds elements of assembly 24, and which is herein assumed to comprise a spectacle frame, so that structure 54 is also referred to herein as frame 54.

In some embodiments, combiner frames 82A and 82B are fixed to retaining structure 54 and vertical retaining rods 84A and 84B attached to the combiner frames support the optical combiners, so that the combiners are able to rotate about vertical axes defined by the rods. Retaining rods 84A and 84B, and thus combiners 52A and 52B, may be rotated independently of each other about their vertical axes by respective motors 86A and 86B, fixed to frames 82A and 82B. Motors 86, typically stepper motors, are controlled by processor 26 so as to rotate their attached combiners to known, typically different, fixed orientations with respect to their respective combiner frames.

Each optical combiner 52 is configured to at least partially transmit elements of a scene through the combiner, so that a portion 56 of patient 30 (FIG. 1) is assumed to be directly visible through each combiner 52. In addition, each optical combiner 52 is configured to receive a visible radiation transmission derived from a scene, and/or a visual transmission such as a presentation of data or a marker, and to redirect or reflect the transmission back to the eye of professional 22.

Optical combiners of various types are known in the art. One known type uses a semi reflective surface which transmits an image from an image source after it has passed through a set of lenses which correct deformations caused by the semi reflective surface of the combiner. Another known type uses a waveguide which projects the image directly to the eye of the viewer. Herein, by way of example, combiners 52 are assumed to be of the waveguide type.

Generally similar pixelated variable transparency screens 60A and 60B respectively coat a rear side, i.e., the side away from the eyes of professional 22, of combiners 52A, 52B. Screens 60 are active elements of system 20 and are formed of an array of pixels, the opacity of each of the pixels being controlled by processor 26.

Screens 60 are typically, but not necessarily, liquid crystal displays (LCDs) formed of a rectangular array of liquid crystal pixels. Alternatively, screens 60 are formed of MEMS (microelectromechanical systems). Further alternatively, screens 60 are formed of polymer dispersed liquid crystals (PDLCs).

Fixedly attached to arms of frame 54 are generally similar micro-projectors 64A and 64B. Each micro-projector is located and oriented so as to be able to project onto respective combiner 52A and 52B, a scene, and/or a visual indication, in a form suitable for redirection by the combiners to the left or right eye of professional 22. Micro-projectors 64 are active elements, and the projected scenes/indications are provided to the micro-projectors by processor 26. The projection and redirection are configured so that the images seen by the eyes of professional 22, absent any correcting lenses, appear to be at infinity, due to parallel light coming from the combiners and entering the pupils. In some embodiments assembly 24 comprises correcting lenses 88A, 88B which redirect light from combiners 52A, 52B so that the images appear to be closer than infinity to the professional's eyes.

At least one image capturing device 68 is attached to frame 54. In a disclosed embodiment there are two generally similar devices 68A and 68B, respectively aligned to be approximately orthogonal to planar combiners 52A and 52B, so as to be able to capture radiation of respective images of scenes viewed by the left and right eyes of professional 22. Typically, devices 68 comprise cameras configured to capture images of scenes viewed by the professional, including images of marker 18 in the visible spectrum.

In embodiments of the present invention, assembly 24 comprises a sensor 72, also herein termed a camera 72, which is configured to capture images of elements of a scene, including marker 18, in front of assembly 24. The images, which include images of marker 18, are produced from radiation projected by a projector 73 that is in the spectrum detected by camera 72. Projector 73 is located in close proximity to camera 72, so that radiation from the projector, that has been retroreflected, is captured by camera 72. The camera typically has a bandpass filter configured to block other radiation, such as that projected by surgical lighting. Typically, camera 72 and projector 73 operate in a non-visible region of the spectrum, such as in the near infra-red spectrum. As is described below, at least some retroreflected radiation is received from marker 18, and processor 26 uses the image of the marker produced by camera 72 from the received radiation to track the marker and ROI 34.

An assembly similar to assembly 24 is described in U.S. Pat. No. 9,928,629 to Benishti et al., which is incorporated herein by reference.

Figure 3B:
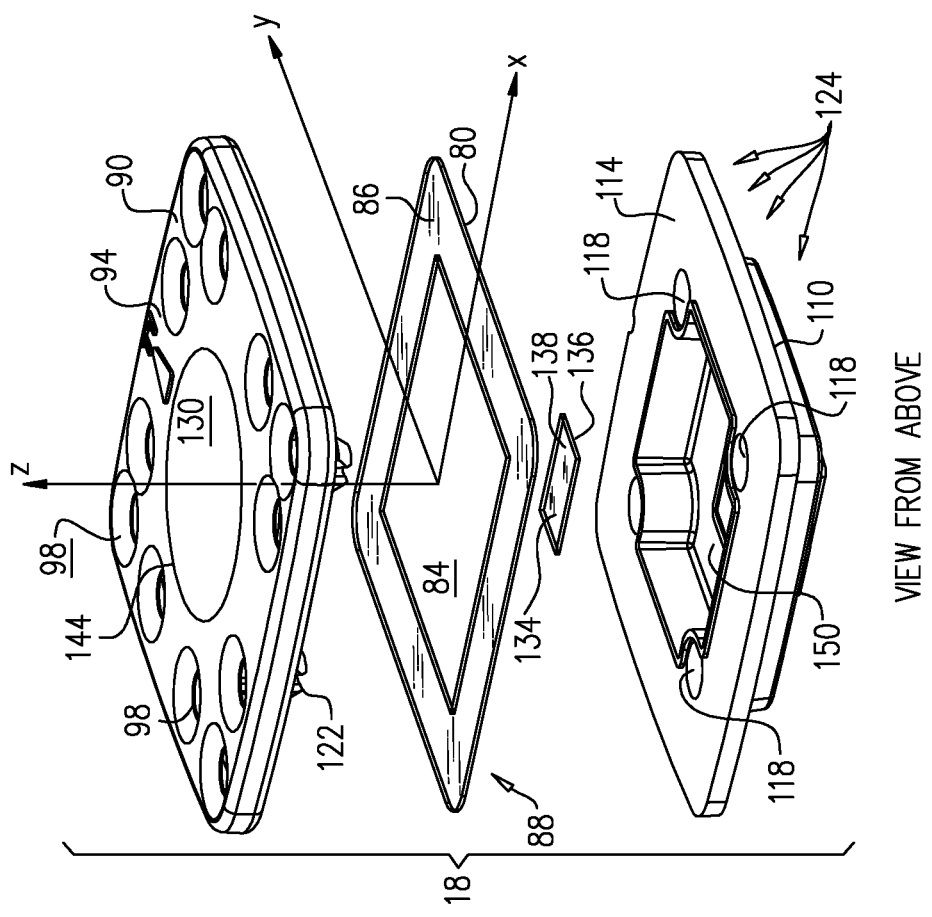
FIG. 3B is a schematic exploded view of the marker as viewed from above.
Figure 3A:
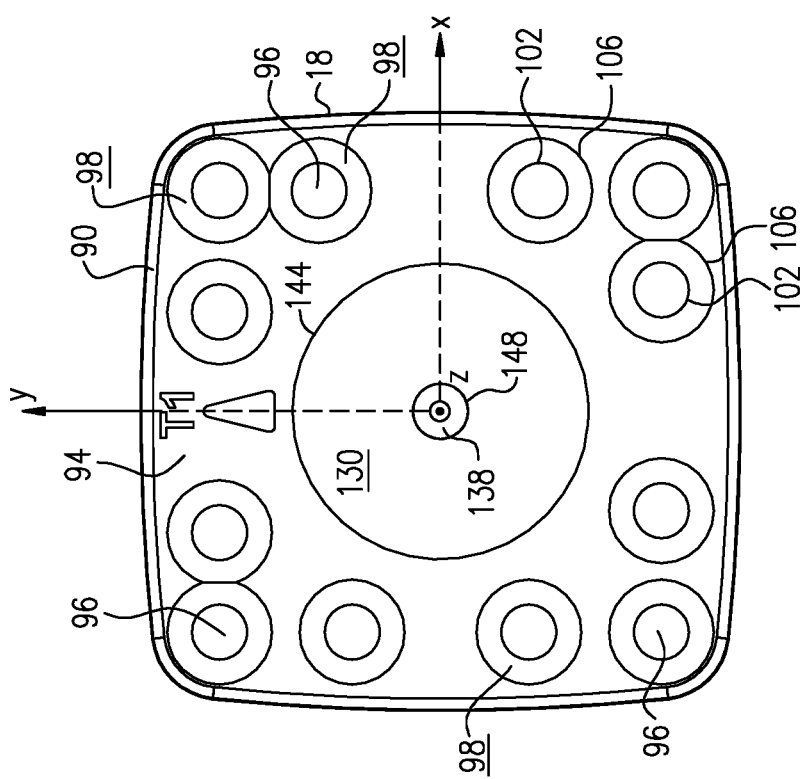
FIG. 3A is a schematic top view of the positioning marker.
Figure 3C:
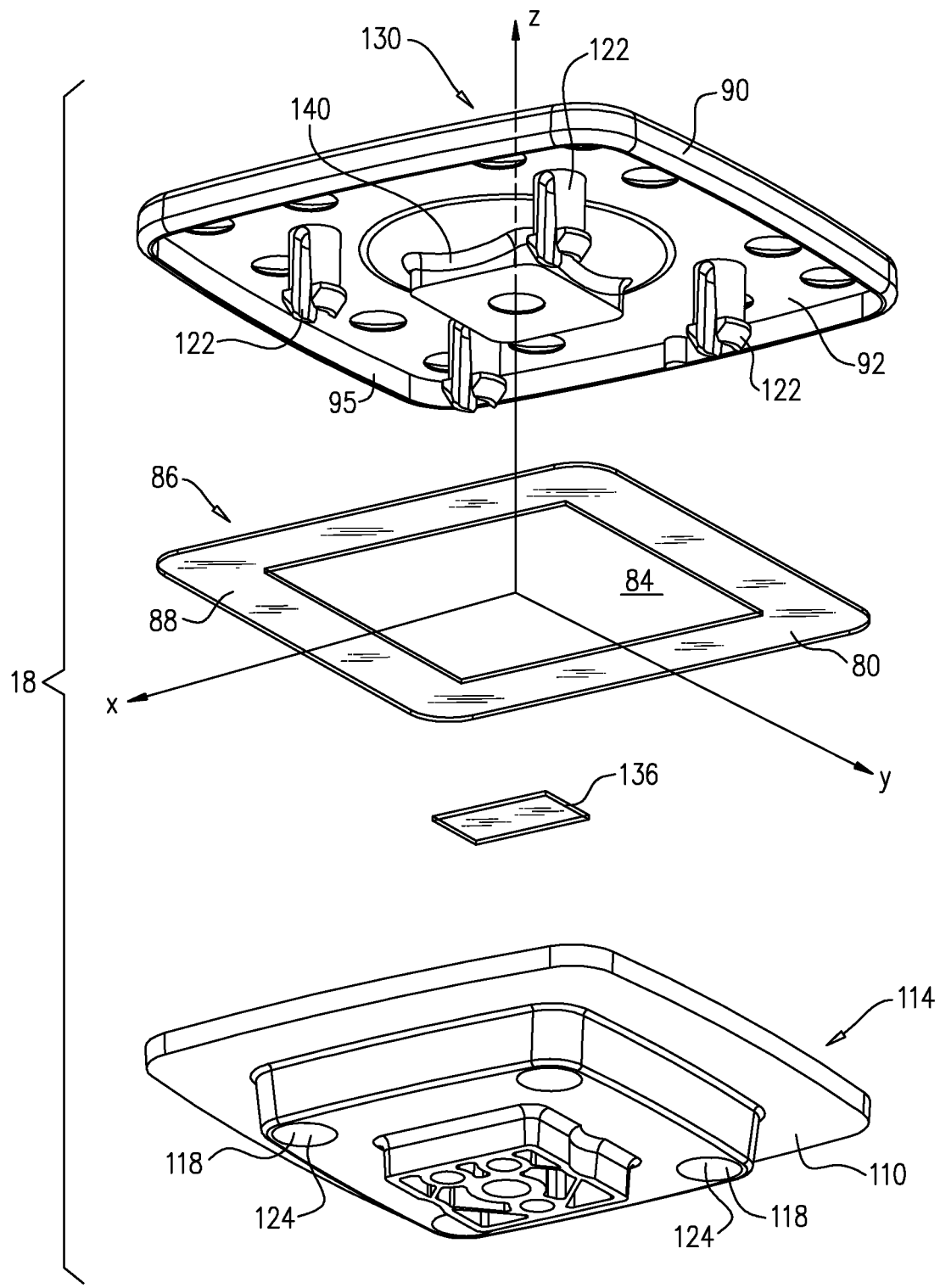
FIG. 3C is a schematic exploded view of the marker as viewed from below, according to an embodiment of the present invention.

FIG. 3A is a schematic top view of marker 18, FIG. 3B is a schematic exploded view of the marker as viewed from above, and FIG. 3C is a schematic exploded view of the marker as viewed from below, according to an embodiment of the present invention. For clarity the views have been drawn on a set of orthogonal xyz axes. In a disclosed embodiment marker 18 comprises a flat planar sheet 80 having a generally rectangular shape and a generally rectangular aperture 84 formed within the sheet. By way of example, an upper surface 86 of sheet 80 is assumed to be on an xy plane of the xyz axes, and the upper surface is assumed have an equation given by equation (1):

$$z=0 \qquad (1)$$

A center of sheet 80 is assumed to be at the origin of the xyz axes, i.e., at a location given by equation (2):

$$x=y=0 \qquad (2)$$

Flat planar sheet 80 has a lower flat plane surface 88.

Sheet 80 acts as a base for marker 18, and is also herein termed base 80. In embodiments of the present invention upper surface 86 of base 80 is retroreflective, and in one embodiment the surface is formed to be retroreflective by adhering retroreflective tape to the upper surface. However, other methods, such as covering with retroreflective paint, for making surface 86 retroreflective will be apparent to those having skill in the art, and all such methods are assumed to be within the scope of the present invention.

Fitted over, and fastened to, base 80 is an inflexible opaque base cover 90, which has a lower plane surface 92 and an upper surface 94. When cover 90 is fastened to base 80, as described below, surface 92 of the cover mates with upper surface 86 of the base.

Cover 90 has a plurality of openings 98, within the cover, which penetrate the top and bottom surfaces of the cover. Openings 98 are substantially congruent to each other, and each opening has the form of a right conical frustum, terminating in a first opening 102 in upper surface 94, and a second opening 106, smaller than opening 102 and herein termed smaller opening 106, in lower plane surface 92. Typically, as shown the figure and as assumed for clarity and simplicity in the following description, openings 102 and 106 are circular. However, embodiments of the present invention comprise other shapes for the openings, such as regular or irregular polygons, and all such shapes are assumed to be comprised within the scope of the present invention.

When cover 90 is fastened to base 80, surface 92 of the cover mates with the retroreflective upper surface of base 80, and smaller circular openings 106 contact base 80, forming retroreflective circles 96, herein termed retroflectors 96. By way of example, the figures illustrate cover 90 as having twelve openings, through each of which the retroreflective upper surface of base 80 is visible, but it will be understood that embodiments of the present invention may have fewer or more than twelve openings.

In one embodiment the centers of retroflectors 96 are formed on a square having a center on the z-axis. However, the spacing of the retroflectors on the square is configured to be non-symmetrical, so that processor 26 may determine a unique orientation of marker 18 from images of the retroflectors. In embodiments where the centers of retroflectors 96 are not formed on a square, the spacing of the retroflectors is also configured so that processor 26 may determine a unique orientation of marker 18 from images of the retroflectors.

By implementing openings 98 as frusta, it will be appreciated that the retroreflective upper surface of base 80 is visible, through the openings, from many different directions. This visibility facilitates the ability of processor 26 to track marker 18 using camera 72 if there is relative motion between the camera and the marker, for example if professional 22 moves.

The inventors have found that accurate tracking of marker 18, using images of the retroreflective upper surface formed by smaller circular openings 106, is contingent on accurate and consistent positioning of the smaller circular openings with respect to each other. Such accurate and consistent positioning is facilitated by separately producing the openings in the cover, and then attaching the base retroreflective surface to the cover, as in embodiments of the present invention. For example, in an embodiment where the cover is a square of approximately 54 mm side, the tolerances on the dimensions of openings 102 and 106 are +/−150 microns or less, and the angles of the frusta forming the openings have tolerances of 0.5° or less.

In order to fasten base 80 to cover 90, marker 18 comprises a cover retainer 110 which has an upper flat plane surface 114. When marker 18 is assembled, the upper flat surface of the cover retainer mates with lower surface 88 of marker base 80. Also, for assembly, cover 90 comprises a lip 95 an inner edge of which mates with a perimeter of retainer 110. In addition, and as described above, when marker 18 is assembled upper retroreflective surface 86 of base 80 mates with lower plane surface 92 of cover 90.

In addition, cover retainer 110 comprises one or more retainer connecting elements 118, which align with cover connecting elements 122 in cover 90. By way of example marker 18 comprises four elements 118 and four elements 122.

Retainer connecting elements 118 comprise cylindrical holes, also herein termed holes 118, which penetrate retainer 110, and cover connecting elements 122 comprise sprung anchors, also herein termed anchors 122, which are dimensioned to align with and penetrate holes 118.

In the assembled form of marker 18, i.e., when base 80 is fastened to cover 90 and cover retainer 110 mates with the lower surface of the base, anchors 122 hold the three entities (the cover, the base, and the cover retainer) fixedly in place. In order to act as marker anchors, anchors 122 are dimensioned so that in a compressed form they are able to penetrate holes 118. The holes and the anchors are further dimensioned to permit the anchors to expand to an uncompressed form when the base, the cover and the cover retainer are in their assembled state, so as to fixedly hold the marker elements in place. Typically, the elements of marker 18 may "snap" together, by anchors 122 reverting to their uncompressed form and engage ledges 124 in holes 118, by applying moderate pressure to the cover and the cover retainer.

Connecting elements for marker 18, other than the holes and anchors described above, will be apparent to those having skill in the art, and all such connecting elements are assumed to be comprised within the scope of the present invention.

Smaller circular openings 106, and the sections of the retroreflective upper surface exposed by the openings, are in a single plane, having an equation given by equation (1).

To further facilitate tracking of marker 18, the marker comprises an additional opening 130 in cover 90, and an associated additional retroreflective surface 134 formed on an additional sheet 136. Retroreflective surface 134 is typically formed in substantially the same manner as retroreflective surface 86, for example by adhering retroreflective tape to surface 134.

In some embodiments, rather than having an additional sheet upon a surface of which retroreflective material is formed, additional sheet 136 may be implemented as adhesive retroreflecting tape that is adhered to an internal surface of recessed portion 150 (described further below) of cover retainer 110. For clarity in the following description additional sheet 136 is assumed to have retroreflective material formed on surface 134, and those having ordinary skill in the art will be able to adapt the description, mutatis mutandis, for the case when sheet 136 is implemented as adhesive reflecting tape.

As explained below, additional opening 130 and additional retroreflective surface 134 are configured to form a section 138 of the additional retroreflective surface that is in a different plane from the plane of sections of the retroreflective upper surface formed by openings 106, i.e., from the plane defined by equation (1). Section 138 is in an xy plane indented or elevated from the plane of equation (1), and thus has an equation given by equation (3):

$$z=n \quad (3)$$

where n is a non-zero number.

Typically section 138 is formed to be circular, and for simplicity in the following description it is considered to be circular. In the embodiment described above where the centers of retroreflectors 96 are on a square, section 138 is configured to be symmetrical with the square, i.e. to be located on the z-axis.

In the embodiment illustrated in FIGS. 3A, 3B, 3C section 138 is indented from the plane of openings 106, so that n is a negative number.

Additional opening 130 is formed, like openings 98, as a right conical frustum, and the opening is formed in a lower, downwardly-protruding, section 140 of cover 90. In section 140 opening 130 has a first circular opening 144 in upper surface 94, and a second, smaller, circular opening 148 in a lower surface of downwardly-protruding section 140. The frustum formed by additional opening 130 has a different depth from the depths of the frusta of openings 98.

When marker 18 is assembled, section 140 protrudes through aperture 84 of base 80, and enters into a recessed portion 150 of cover retainer 110. Sheet 136, with its retroreflective surface uppermost, is cemented onto an upper surface of portion 150. Smaller circular opening 148 and the upper surface of portion 150 are dimensioned so that when marker 18 is assembled, with its elements fixed in place, smaller circular opening 148 contacts sheet 136, and circular section 138 and its retroreflective surface is exposed by the circular opening and is visible through opening 130. Circular section 138 is herein also termed retroreflector 138.

By forming opening 130 as a frustum, retroreflector 138 is visible (as with retroflectors 96 of openings 98) from many different directions, so facilitating the ability of processor 26 to track marker 18 using camera 72. In the square embodiment referred to above, smaller circular opening 148 has a diameter of 5 mm, and opening 130 is a circular conical frustum having a conical angle of 120°.

In the embodiments described above the positions of the connecting elements (elements 118 and 122) are selected so as not to interfere with the functioning of retroreflectors 96 and 138. The positions of the connecting elements are provided by way of example, and those having ordinary skill in the art will be aware of other connecting element positions that do not interfere with the functioning of the retroreflectors. All such positions are assumed to be comprised within the scope of the present invention.

While the description above has addressed using tracking marker 18 to track ROI 34, those having ordinary skill in the art will be able to adapt the description, mutatis mutandis, if the marker is used for other tracking purposes, such as being attached to a tool in order to track the tool.

FIGS. 4A, 4B, and 4C are schematic diagrams of a cover 290 for a marker 218, according to an alternative embodiment of the present invention. FIG. 4A is a top view of the cover, FIG. 4B is a perspective view of the cover, and FIG. 4C is a cross-section of the cover taken along a line 4C-4C of FIG. 4A. Apart from the differences described below, the operation of cover 290 is generally similar to that of cover (FIGS. 3A, 3B, and 3C), and elements indicated by the same reference numerals in both covers are generally similar in construction and in operation.

Rather than the additional opening 130 of cover 90, which forms an indented section 138, cover 290 comprises a support 228 for an elevated additional opening 230. Support 228 protrudes from cover 290. Opening 230, herein assumed to be generally similar to openings 98, is a right conical frustum terminating in a first opening 202 and a second opening 206, smaller than the first opening.

Second opening 206 is formed in a lower internal plane surface 292 of support 228.

To form marker 218 a base substantially identical to base 80, and having a retroreflective upper surface as described above for base 80, is fastened to a lower plane surface 294 of cover 290. A sheet similar to sheet 136 is fit to surface 292, the sheet having an upper reflective surface, visible through opening 206, and having dimensions modified from those for marker 18 so as to fit within support 228. A plane of the modified sheet aligns with lower internal plane surface 292. Marker 218 also comprises a cover retainer similar to retainer 110, but modified to support modified sheet 136 in contact with surface 292. The modifications referred to above will be apparent to those having ordinary skill in the art, and may be implemented without undue experimentation.

Figure 5:
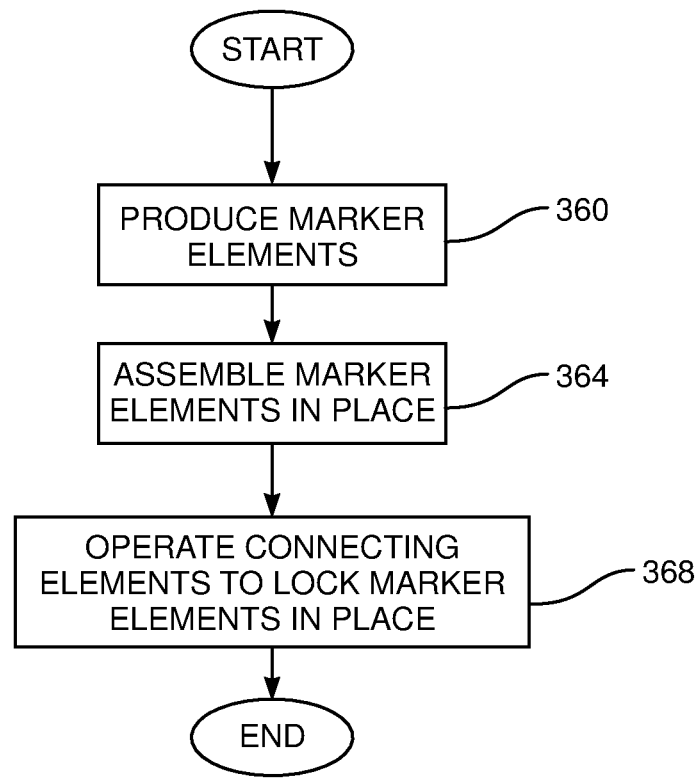
FIG. 5 is a flowchart of steps performed in producing a positioning marker, according to an embodiment of the present invention.

FIG. 5 is a flowchart of steps performed in producing marker 18, according to an embodiment of the present invention. Those having ordinary skill in the art will be able to adapt the following description, mutatis mutandis, for producing marker 218. In an initial step 360, the separate marker elements, i.e., base 80, base cover 90, cover retainer 110, and sheet 136 are produced according to predetermined dimensions. Base 80 and sheet 136 may be produced by any convenient means known in the art, for example by stamping, and their upper surfaces may be made retroreflective as described above.

Cover 90 may be produced, for example, from a mold. Other methods for producing the cover will be apparent to those having skill in the art, but the method chosen should ensure that there is accurate and consistent positioning of smaller circular openings 106 and 148 with respect to each other. The material for the cover is typically an inflexible plastic such as polyimide.

In an initial assembly step 364 the marker elements are assembled generally as illustrated in FIGS. 3B and 3C. Typically in this step sheet 136, with its retroreflective surface uppermost, may be adhered to an upper surface of recessed portion 150 of cover retainer 110.

In a final assembly step 368, moderate pressure is applied to the upper surface of cover 90 and the lower surface of retainer 110, so that anchors 122 engage ledges 124 so as to fixedly connect all the elements of the marker. In the final assembly, base 80 and sheet 136 are effectively "sandwiched" between cover 90 and cover retainer 110.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A positioning marker, comprising:
   a base, comprising a planar sheet configured in a first plane, the planar sheet having a retroreflective surface;
   a cover, which is fitted over and fastened to the base and has a plurality of openings through which the retroreflective surface is visible, the plurality of openings generating respective retroreflectors in the first plane, from the retroreflective surface, when the cover is fastened to the base;
   an additional opening in the cover; and
   an additional sheet, having an additional retroreflective surface configured in a second plane parallel to and distinct from the first plane, so that the additional retroreflective surface is visible through the additional opening when the cover is fastened to the base.

2. The positioning marker according to claim 1, wherein the openings are right conical frusta.

3. The positioning marker according to claim 2, wherein the frusta terminate in respective first surface openings and second surface openings smaller than the first surface openings, and wherein the second surface openings contact the retroreflective surface when the cover is fastened to the base, forming the respective retroreflectors.

4. The positioning marker according to claim 3, wherein the respective retroreflectors are arranged on a flat plane.

5. The positioning marker according to claim 1, wherein the retroreflective surface comprises a base flat surface, and wherein the cover comprises a cover flat surface which mates with the base flat surface when the cover is fastened to the base, so that respective sections of the openings contact the retroreflective surface.

6. The positioning marker according to claim 1, wherein the additional opening is a right conical frustum.

7. The positioning marker according to claim 6, wherein the base comprises an aperture formed therewithin, and wherein the right conical frustum protrudes through the aperture when the cover is fastened to the base.

8. The positioning marker according to claim 1, and comprising a support protruding from the cover, the support comprising a support plane, aligned with the second plane, configured to fit to the second sheet.

9. The positioning marker according to claim 1, and comprising a cover retainer which is configured to be fixedly connected to the cover and to retain the base in fixed contact with the cover, so as to fasten the base to the cover.

10. The positioning marker according to claim 9, wherein the base comprises an aperture formed therewithin, the cover comprises a first connecting element, and the cover retainer comprises a second connecting element mating with the first connecting element so as to fasten the cover to the cover retainer and the base, and wherein at least one of the connecting elements protrudes through the aperture.

11. The positioning marker according to claim 1, wherein the retroreflective surface comprises at least one of retroreflective tape and retroreflective paint.

12. A method for producing a positioning marker, comprising:
    forming a retroreflective surface on a base comprising a planar sheet configured in a first plane;
    fitting a cover over and fastening the cover to the base, wherein the cover has a plurality of openings through which the retroreflective surface is visible, the plurality of openings generating respective retroreflectors in the first plane, from the retroreflective surface, when the cover is fastened to the base;
    providing an additional opening in the cover; and
    providing an additional sheet, having an additional retroreflective surface configured in a second plane parallel to and distinct from the first plane, so that the additional retroreflective surface is visible through the additional opening when the cover is fastened to the base.

13. The method according to claim 12, wherein the openings are right conical frusta.

14. The method according to claim 13, wherein the frusta terminate in respective first surface openings and second surface openings smaller than the first surface openings, and wherein the second surface openings contact the retroreflective surface when the cover is fastened to the base, forming the respective retroreflectors.

15. The method according to claim 14, wherein the respective retroreflectors are arranged on a flat plane.

16. The method according to claim 12, wherein the retroreflective surface comprises a base flat surface, and wherein the cover comprises a cover flat surface which mates with the base flat surface when the cover is fastened to the base, so that respective sections of the openings contact the retroreflective surface.

17. The method according to claim 12, wherein the additional opening is a right conical frustum.

18. The method according to claim 17, wherein the base comprises an aperture formed therewithin, and wherein the right conical frustum protrudes through the aperture when the cover is fastened to the base.

19. The method according to claim 12, wherein the cover comprises a support protruding therefrom, the support comprising a support plane, aligned with the second plane, configured to fit to the second sheet.

20. The method according to claim 12, and comprising providing a cover retainer which is configured to be fixedly connected to the cover and to retain the base in fixed contact with the cover, so as to fasten the base to the cover.

21. The method according to claim 20, wherein the base comprises an aperture formed therewithin, the cover comprises a first connecting element, and the cover retainer comprises a second connecting element mating with the first connecting element so as to fasten the cover to the cover retainer and the base, and wherein at least one of the connecting elements protrudes through the aperture.

22. The method according to claim 12, wherein the retroreflective surface comprises at least one of retroreflective tape and retroreflective paint.

* * * * *

UNITED STATES PATENT AND TRADEMARK OFFICE
CERTIFICATE OF CORRECTION

PATENT NO. : 10,939,977 B2
APPLICATION NO. : 16/199281
DATED : March 9, 2021
INVENTOR(S) : Daniel Messinger, Stuart Wolf and Nissan Elimelech It is certified that error appears in the above-identified patent and that said Letters Patent is hereby corrected as shown below:

In the Drawings

Sheet 3/6, Fig. 3A, the reference numbers 102 and 106 should be reversed so that the number 106 is applied to the smaller openings and number 102 is applied to the larger openings.

Sheet 5/6, Fig. 4A, the reference numbers 102 and 106 should be reversed so that the number 106 is applied to the smaller openings and number 102 is applied to the larger openings.

In the Specification

Column 4, Line 29, should read "sandwiched between the cover retainer and the".

Column 7, Line 18, should read "assumed to have an equation given by equation (1):".

Column 7, Line 47, should read "Typically, as shown in the figure and as assumed for clarity and".

Signed and Sealed this
Twenty-ninth Day of August, 2023

Katherine Kelly Vidal
*Director of the United States Patent and Trademark Office*